(12) United States Patent
Maruta

(10) Patent No.: US 12,274,579 B2
(45) Date of Patent: Apr. 15, 2025

(54) RADIATION IMAGING SYSTEM AND STORAGE MEDIUM

(71) Applicant: KONICA MINOLTA, INC., Tokyo (JP)

(72) Inventor: Yuuichi Maruta, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 222 days.

(21) Appl. No.: 17/826,288

(22) Filed: May 27, 2022

(65) Prior Publication Data

US 2022/0395247 A1 Dec. 15, 2022

(30) Foreign Application Priority Data

Jun. 11, 2021 (JP) .................. 2021-097723

(51) Int. Cl.
*A61B 6/00* (2024.01)
*A61B 6/42* (2024.01)
*A61B 6/46* (2024.01)

(52) U.S. Cl.
CPC ............ *A61B 6/542* (2013.01); *A61B 6/4208* (2013.01); *A61B 6/4291* (2013.01); *A61B 6/463* (2013.01); *A61B 6/465* (2013.01); *A61B 6/469* (2013.01); *A61B 6/545* (2013.01)

(58) Field of Classification Search
CPC ......... A61B 6/00; A61B 6/542; A61B 6/4291; A61B 6/463; A61B 6/465; A61B 6/469; A61B 6/545; A61B 6/4208; A61B 6/4233; A61B 6/486
See application file for complete search history.

(56) References Cited

U.S. PATENT DOCUMENTS

| | | |
|---|---|---|
| 10,485,504 B2 | 11/2019 | Arima |
| 10,898,148 B2 | 1/2021 | Taneda |
| 2018/0333128 A1 | 11/2018 | Obara |
| 2020/0273165 A1 | 8/2020 | Kanamori |
| 2022/0054100 A1 | 2/2022 | Hiroshige et al. |

FOREIGN PATENT DOCUMENTS

| | | |
|---|---|---|
| JP | 2017144075 A | 8/2017 |
| JP | 2018000792 A | 1/2018 |
| JP | 2018192129 A | 12/2018 |
| JP | 2020130796 A | 8/2020 |
| JP | 6860113 B1 | 3/2021 |
| WO | 2011074471 A1 | 6/2011 |

OTHER PUBLICATIONS

Japanese Office Action (and an English language translation thereof) dated Jan. 14, 2025, issued in counterpart Japanese Application No. 2021-097723.

*Primary Examiner* — Jurie Yun

(74) *Attorney, Agent, or Firm* — Holtz, Holtz & Volek PC

(57) ABSTRACT

A radiation imaging system includes a hardware processor. The hardware processor calculates an exposure index representative value of a radiation image based on the radiation image including a plurality of frame images. The hardware processor is capable of setting a target value of an exposure index differently for each imaging mode.

2 Claims, 2 Drawing Sheets

RADIATION IMAGING SYSTEM AND STORAGE MEDIUM

CROSS-REFERENCE TO RELATED APPLICATIONS

The entire disclosure of Japanese Patent Application No. 2021-097723 filed on Jun. 11, 2021 is incorporated herein by reference in its entirety.

BACKGROUND

Technological Field

The present invention relates to a radiation imaging system and a storage medium.

Description of the Related. Art

Different from conventional film, in a digital radiation detector, image processing (for example, gradation processing) is performed automatically on a generated radiation image, and brightness and contrast are maintained in a constant state. Therefore, it became difficult for the user to determine from the obtained radiation image whether the radiation in the dose intended by the user reached the radiation detector.

In the past, the manufacturers of the radiation detectors each provided their own index (exposure index) in order to evaluate the dose that reached the radiation detector. However, lately, a unified index called Exposure-Index (hereinafter referred to as EI) is used as a standard for determination.

Whether the dose of radiation intended by the user reached the radiation detector is determined by judging the degree of how different (deviation index, hereinafter referred to as DI) the calculated EI is from a target value of the EI (Target Exposure Index, hereinafter referred to as EIT) determined in advance for each imaging condition. Therefore, techniques have been proposed conventionally to appropriately set the EIT or to revise the EIT as necessary.

For example, JP 2018-192129 focuses on the point that the dose that reaches the radiation detector (EI) changes depending on whether there is a grid, and describes a radiation imaging apparatus that selects a different EIT depending on whether there is a grid.

Conventionally, as described in JP 2020-130796, one light exposure index is calculated for one radiation image.

In JP 2018-000792, one exposure index is calculated for one combined image.

Conventionally, in simple X-ray imaging for obtaining still images, the dose is managed in order to optimize a dose of radiation exposure. Specifically, conventionally, each time imaging is performed, image data obtained in one occasion of imaging is stored corresponded with the dose of radiation used in this one occasion of imaging.

In dynamic imaging for obtaining a dynamic image including a plurality of frame images, management of the dose is performed similar to simple imaging. That is, the image data obtained in one occasion of imaging the dynamic image is stored corresponded with the dose of radiation used in this one occasion of imaging.

In simple imaging, for example, JP 2017-144075 describes a technique to store and manage image data corresponded with the dose of radiation used in the imaging when the imaging fails and the image results in failure.

JP 6860113 describes generating a dynamic image including some of the frame images extracted among all of the frame images in the dynamic imaging and calculating the total dose before extracting some of the frame images based on a Numerical Dose Determination (NDD) method or based on a number of pulses.

SUMMARY

According to the conventional techniques, when the radiation image (dynamic image or successive still images) including a plurality of frame images is imaged, the calculation of the dose of radiation was not always easy or appropriate.

The present invention is conceived in view of the above problems, and the purpose of the present invention is to optimize the calculation of the dose of radiation when the radiation image including a plurality of frame images is imaged to be more simple. To achieve at least one of the abovementioned objects, according to an aspect of the present invention, a radiation imaging system reflecting one aspect of the present invention includes: a hardware processor, wherein the hardware processor calculates an exposure index representative value of a radiation image based on the radiation image including a plurality of frame images, and wherein the hardware processor is capable of setting a target value of an exposure index differently for each imaging mode.

A radiation imaging system includes: a hardware processor, wherein the hardware processor calculates a radiation dose in imaging to obtain a radiation image including a plurality of frame images, and wherein the hardware processor calculates the radiation dose corresponding to a cumulative amount of all imaged frames based on a dose index calculated from at least one of an imaging condition which is applied when imaging is performed and which is received from a radiation generating apparatus and distance information showing a distance to a subject and based on a number of pulses which is a number of times that the radiation generating apparatus generates radiation in a pulsed state to obtain the frame image when imaging is performed.

A non-transitory computer-readable storage medium storing a program causing a computer to perform: calculating an exposure index representative value of a radiation image based on the radiation image including a plurality of frame images, and being capable of setting a target value of an exposure index to be different for each imaging mode.

A non-transitory computer-readable storage medium storing a program causing a computer to perform: calculating a radiation dose in imaging to obtain a radiation image including a plurality of frame images, and calculating the radiation dose equivalent to a cumulative amount of all of the frames that are imaged based on a dose index calculated from at least one of an imaging condition which is applied at the time of imaging and which is received from a radiation generating apparatus and distance information showing a distance to a subject, and based on a number of pulses which is a number of times the radiation generating apparatus generates the radiation in a pulsed state to obtain the frame image when imaging is performed.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

The radiation imaging system according to one embodiment of the present invention is described with reference to the drawings. However, the scope of the present invention is not limited to the scope described in the embodiments and drawings.

Figure 1:
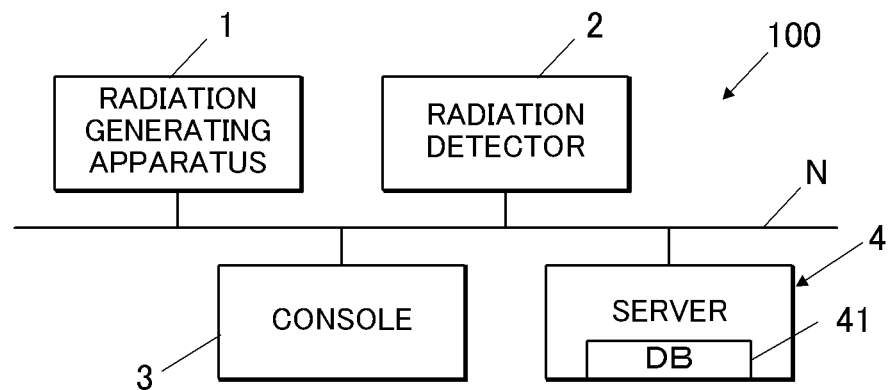
FIG. 1 is a block diagram showing a radiation imaging system according to an embodiment of the present invention.

First, the schematic configuration of a radiation imaging system 100 according to the present embodiment is described. FIG. 1 is a block diagram showing a radiation imaging system 100.

As shown in FIG. 1, the radiation imaging system 100 according to the present embodiment includes a radiation generating apparatus 1, a radiation detector 2, a console 3, and a server 4.

The above units are able to communicate with each other through a communication network N.

The radiation imaging system 100 is able to connect to a Hospital Information System (HIS), a Radiology Information System (RIS), a Picture Archiving and Communication System (PACS), an image analysis apparatus, and the like (all not shown).

Although not shown, the radiation generating apparatus 1 includes a generator that applies voltage according to a radiation emitting condition (tubular voltage, tubular current, radiation emitting duration (mAs value), etc.) set in advance based on operation of an emitting instruction switch, a radiation source that generates radiation (for example, X-ray) when voltage from the generator is applied in a dose according to the applied voltage and the like.

The radiation generating apparatus 1 generates radiation (for example, X-ray) in a manner according to the imaged radiation image (still image, moving image).

The radiation generating apparatus 1 may be provided fixed in an imaging room or may be included in a mobile medical vehicle together with the console 3 so as to be able to move.

Although illustration is omitted, the radiation detector 2 includes, a substrate including two-dimensionally (in a matrix) aligned pixels including a radiation detecting element that generates charge according to the dose when the radiation is received and a switch element that accumulates and discharges charge, a scanning circuit that switches on and off of each switch element, a read out circuit that reads out an amount of charge discharged from each pixel as a signal value, a controller that generates a radiation image from the plurality of signal values read out from the readout circuit, an outputter that outputs data of the generated radiation image outside, and the like.

Then, the radiation detector 2 synchronizes with the timing that the radiation is emitted from the radiation generating apparatus 1 and generates the radiation image according to the emitted radiation.

The radiation detector 2 may be an indirect type radiation detector that includes a scintillator, etc. and the scintillator may be used to convert the emitted radiation to light in another wave length such as visible light. With this, the charge is generated according to the converted light. Alternatively, the radiation detector 2 may be a direct type radiation detector that directly generates charge from the radiation without using the scintillator, etc.

The radiation detector 2 may be a dedicated device formed as one with an imaging stage, or may be a portable type (cassette type).

The console 3 is included in an image processing apparatus, an electronic device, and the like. The console 3 is a PC or a dedicated device.

By using the console 3, various imaging conditions (tubular voltage, tubular current, radiation emitting duration (mAs value), frame rate, physique of subject, whether there is grid, etc.) can be set in the imaging apparatus based on imaging order information obtained from other systems (HIS, RIS, etc.) or operation by the user.

The server 4 includes a PC or a dedicated apparatus, a virtual server in a cloud, and the like.

The server 4 includes a database 41.

According to the present embodiment, a database 41 is provided in the server 4 independent from the console 3, etc., but the database 41 may be provided in the console 3 or in other apparatuses provided in the radiation imaging system 100.

When another system such as PACS is connected to the radiation imaging system 100, the database may be provided in another system.

In the radiation imaging system 100 according to the present embodiment, the radiation source of the radiation generating apparatus 1 is positioned facing the radiation detector 2 with a space in between, and the radiation is emitted from the radiation source to the subject positioned between the above. With this, the radiation image of the subject can be imaged.

When the radiation image is a still image, the radiation is emitted and the radiation image is generated only once for every one operation of imaging (pressing of the emitting instruction switch). When the radiation image is a moving image, the emitting of the pulsed radiation and the generating of the frame image is repeated a plurality of times within a short amount of time (for example, 15 times for every second) for every one operation of imaging.

Figure 2:
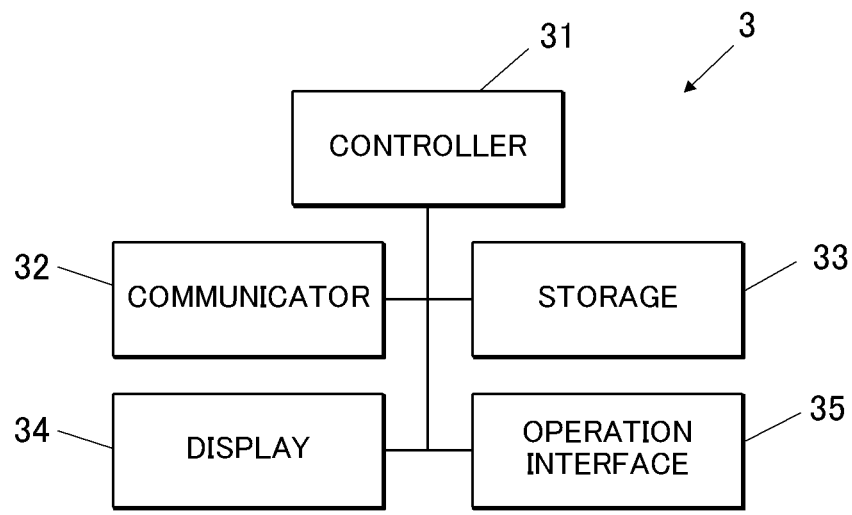
FIG. 2 is a block diagram showing a console (image processing apparatus) including a radiation imaging system shown in FIG. 1.
Figure 3:
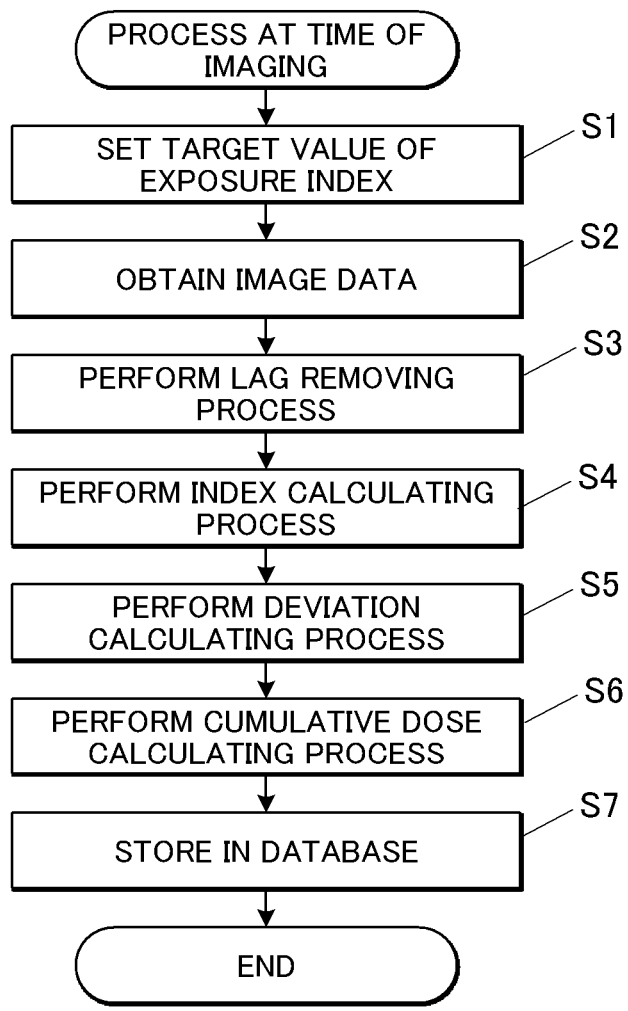
FIG. 3 is a flowchart showing a processing performed by the console shown in FIG. 2 when imaging is performed.

Next, the specific configuration of the console 3 included in the radiation imaging system 100 is described. FIG. 2 is a block diagram showing the console 3, and FIG. 3 is a flowchart showing the processing performed by the console 3 when the imaging is performed.

As shown in FIG. 2, the console 3 according to the present embodiment includes a controller 31 (hardware processor), a communicator 32, a storage 33, a display 34, and an operation interface 35.

The above units 31 to 35 are connected to each other electrically.

The controller 31 includes a CPU (Central Processing Unit), a RAM (Random Access Memory), and the like.

The CPU of the controller 31 reads various programs stored in the storage 33 and deploys the program in the RAM. The CPU of the controller 31 performs various processes according to the deployed program, and centrally controls the operations in each unit of the console 3.

The communicator 32 includes a communication module, etc.

The communicator 32 transmits and receives various signals and various data, to and from other devices, connected via the communication network N (LAN (local area network), WAN (wide area network), the internet, etc.).

The storage 33 includes a non-volatile semiconductor memory, a hard disk, or the like.

The storage 33 stores various programs executed by the controller 31, parameters necessary for executing the programs, and the like.

The storage 33 according to the present embodiment stores a plurality of target values of the exposure index for each imaging site, and for each imaging condition (for example, at least one of the following, physique of subject (normal, fat, skinny, etc.), whether there is a grid, whether scattering correction process is performed).

The storage 33 may be able to store the radiation image.

The display 34 includes a display apparatus that displays an image, such as an LCD (Liquid Crystal Display) or a CRT (Cathode Ray Tube), a light emitting lamp (LED, etc.), a speaker that outputs sounds, a vibrator that vibrates, and the like.

The operation interface 35 includes a keyboard having cursor keys, number keys, and various function keys, a pointing device such as a mouse, and a touch panel layered on a front surface of the display apparatus.

The operation interface 35 outputs to the controller 31 a control signal according to the operation performed by the user.

The controller 31 of the console 3 as described above includes a function to perform the processing performed at the time of imaging as shown in FIG. 3, triggered when a predetermined operation to start is performed such as power being turned on.

For example, as shown in FIG. 3, in the process performed when the imaging is performed according to the present embodiment, first, the target value of the exposure index is set (step S1).

Such "exposure index" corresponds to the Exposure Index (EI) that shows the dose that reached the radiation detector 2. Alternatively, the exposure index may be related to noise (S/N (SN ratio), scattered ray content percentage) different from the Exposure Index (EI) used in the past as described in JP 2020-130796.

The "target value of the exposure index" is a numeric value considered to be the preferable value achieved by the exposure index calculated after imaging.

The controller 31 functions as an exposure target setter and is able to set the target value of the exposure index that is different for each imaging mode. The imaging mode includes a still image imaging mode and a dynamic image imaging mode. The controller 31 is able to set the target value of the exposure index to be different for at least the still image imaging mode and the dynamic imaging mode.

The dose that needs to reach the radiation detector 2 may be different depending on the type of image analysis process performed after imaging. For example, in the image analysis, the state of the joints, the amount of movement of the diaphragm during breathing, and the state of blood flow are clarified. Here, even if the same chest portion is imaged, the dose that needs to reach the radiation detector 2 to analyze the motion amount of the diaphragm and the dose that needs to reach the radiation detector 2 to analyze the state of the blood flow are different. Specifically, a high S/N ratio is not required in the dose that reaches the radiation detector 2 in order to see the motion amount, but a high S/N ratio is required when a fine signal such as blood flow information is analyzed. As described above, even if the same site is imaged, the target value of the dose that needs to reach the radiation detector 2 is different depending on the purpose of diagnosis. Such difference in the imaging conditions depending on the purpose of diagnosis is also included in the imaging mode. The controller 31 is able to set the target value of the exposure index different for each imaging mode. The controller 31 sets the imaging mode and also sets the target value of the exposure index considered to be desirable for each set imaging mode.

After the target value is set, the target value is applied to the radiation generating apparatus 1 and the radiation detector 2, and the radiation image is imaged. The still image imaging is performed when the still image imaging mode is set, and the dynamic imaging is performed when the dynamic imaging mode is set. During the imaging, the console 3 is on standby.

The process in step S1 can be performed as a process independent from the process performed when imaging is performed. Here, when the predetermined start operation is performed or the image data of the radiation image is obtained, the process in the later described step S2 or step S3 is performed.

After the imaging is performed, the image data of the radiation image is obtained (step S2).

Here, "obtain" includes receiving the image data from other apparatuses (radiation detector 2, etc.) and reading the image data from a storage medium. When the storage 33 of the console 3 is configured to be capable of storing the image data, "obtain" includes reading the image data stored in the storage 33 after receiving the image data from other apparatuses or obtaining the image data.

After the image data is obtained, the controller 31 functions as the exposure index calculator and performs the index calculating process in which the exposure index and the exposure index representative value are calculated based on the obtained image data (step S4).

Before the controller 31 performs an index calculating process (step S4), the controller 31 performs a lag removing process (step S3). The lag corresponds to a shadow remaining from the previously imaged frame when the dynamic imaging is performed. In the lag removing process (step S3), the controller 31 performs the process to convert the signal value of the frame images to the signal value in which the influence of the lag is removed.

The controller 31 performs the lag removing process (step S3) and calculates the exposure index and the exposure index representative value based on the frame image after the influence of the lag is removed in step S4. The lag removing process does not have to be performed by the controller 31. The image data recorded after the lag removing process may be read out by the controller 31, and the exposure index and the exposure index representative value may be calculated based on the frame image after removing the influence due to the lag. When the influence due to the lag is within an acceptable error range of the exposure index, the lag removing process (step S3) can be omitted in order to shorten processing time.

In the index calculating process (step S4), first, the controller 31 sets a region of interest (ROI) in the radiation image. The region of interest is set in the entire or in a portion of the radiation image.

When a plurality of frame images are included in the obtained image data, the controller 31 calculates the exposure index of each frame included in the plurality of frame images and calculates the exposure index representative value of the radiation image based on the radiation image including the plurality of frame images. That is, the controller 31 calculates the exposure index representative value based on a set of the exposure indices of the frame images. The controller 31 calculates at least one among the maximum value, the minimum value, the average value and the median value of the set of exposure indices in the frame images included in the plurality of frame images as the exposure index representative value. The maximum value, the minimum value, the average value and the median value may be the value excluding the outliers or the value can be determined by other statistical methods. When only a single frame image is included in the obtained image data, the controller 31 calculates the exposure index based on the single frame image.

The frame that is used for calculating the exposure index can be narrowed to specific frames. For example, the start of output of the radiation is considered to be unstable. Therefore, the frames after the middle frames may be used in the calculation or the frames in which the subject is not included may be excluded.

The exposure index of the frame image selected as the representative from the plurality of frame images may be the exposure index representative value.

The controller 31 also functions as an image recognizer that recognizes the region of the subject.

For example, when the dynamic imaging of the patient who is the subject is performed, the amount of exposure suitable for the most interested posture of the patient may be the target value of the exposure index. In this case, the frame image corresponding to the most interested patient posture in which the above target value is set may be extracted after imaging and the exposure index of the frame image may be the exposure index representative value of the string of dynamic imaged images. For example, when the dynamic imaging of the side of the lumbar spine is performed, and the patient moves from the back bent to an upright posture, if the image in which the patient is closest to the upright posture is the most interested posture of the patient, the frame image imaging the patient in such posture is extracted by image recognition, and the exposure index of the frame image is to be the exposure index representative value of the string of dynamic imaged images.

The controller 31 may change the region of interest for each frame in the plurality of frame images and calculate the exposure index for each frame image. Then, the controller 31 may calculate the exposure index representative value based on the set of exposure indices of the frame images. For example, the controller 31 may change and set the region of interest for each frame so as to follow the motion of the patient who is the subject based on the image recognition result.

The controller 31 may set the region of interest to be the entire frame for each frame in the plurality of frame images, and calculate the exposure index for each frame image. Then, the controller 31 may calculate the exposure index representative value based on the set of exposure indices of the frame images. In this case, the image recognition process is not performed so the burden of the computational processing can be reduced.

The controller 31 may set the region of interest to be a portion common according to the motion of the subject recognized by the image recognizer in each frame in the plurality of frame images and calculate the exposure index for each frame image. Then, the controller 31 may calculate the exposure index representative value based on the set of exposure indices of the frame images. For example, in the dynamic imaging to inspect the motion of a joint, if the joint does not go outside a portion of the imaging region, this portion is set as the common region of interest.

The controller 31 functions as a display controller that controls the display of the plurality of frame images.

The controller 31 calculates a deviation index showing a degree of misalignment of the exposure index of each frame image with relation to the target value of the exposure index based on the target value of the exposure index set in step S1 and the exposure indices of the frame images calculated in step S4 (step S5).

The deviation index can be calculated by the method similar to conventional methods of calculating the deviation index. Specifically, the deviation index is calculated by substituting the calculated exposure index and the set target value in the following formula (1).

$$\text{Deviation index} = 10 \, \text{Log}_{10}(\text{exposure index/target value of exposure index}) \quad (1)$$

The controller 31 functions as a display controller. The deviation index corresponding to each frame image can be displayed on the display 34 with a numeric value, and the deviation index can be displayed on the display 34 classified by level with different colors. As a specific display format, when the plurality of frame images are sequentially or simultaneously displayed on the display 34, the deviation index is displayed by a numeric value in a portion inside the frame image or a portion outside the frame image. As the display format according to color, the entire frame image may be colored, a frame of the frame image may be colored, the numeric value of the deviation index corresponding to the frame image may be colored or the background of such numeric value may be colored. The corresponding between the classified level and the color may be, for example, green (or no color) for a small deviation, yellow for a medium deviation, or red for a large deviation. Alternatively, other combinations of colors may be employed.

The controller 31 performs the display of the preview image when the dynamic imaging is performed together with the display of the color according to the classification of the deviation index based on the setting instruction from the operation interface 35. For example, the dynamic imaging is performed at a frame rate of 300 frames/20 seconds. In such dynamic imaging, the controller 31 performs the display of the preview image together with the display of color according to the classification of the deviation index. The user is able to immediately recognize that the deviation index is excessive by the displayed color, and the user is able to perform operation such as to stop the imaging in the middle to avoid the imaging from becoming meaningless.

When the calculation of the exposure index in order to add color to the preview image takes too much time, the calculation method of the exposure index with a low calculation burden can be employed for the display of the preview image. For example, a method in which the region of interest is fixed to be the entire image or a predetermined portion of the image, and the exposure index can be calculated without performing the image recognition process can be employed.

The controller 31 functions as the dose calculator that calculates the dose of radiation in the imaging in order to obtain the radiation image including the plurality of frame images. The controller 31 functions as the dose calculator and performs a cumulative dose calculating process (step S6) that calculates the dose of radiation corresponding to a cumulative dose of all of the imaged frames (hereinafter referred to as "cumulative dose").

The above-described exposure index representative value is equivalent to an amount of one frame. That is, the controller 31 functions as the exposure index calculator and calculates the exposure index representative value equivalent to an amount of one frame.

In contrast, when the controller 31 functions as the dose calculator, the cumulative dose is calculated.

Regarding the dose, it is important to manage the total amount in the imaging. However, if the exposure index is the total dose that reaches the radiation detector 2, this influences the number of images imaged when the dynamic image is imaged. Therefore, if the amount of radiation is managed converted to the equivalent amount of one frame, this becomes easier to use for the user. Moreover, another advantage is that the comparison of the exposure index with the still image can be easily done.

The exposure index shows the dose that reaches the radiation detector 2. In the cumulative dose calculating process (step S6), a dose area product value (DAP value), an entrance dose and an entrance surface dose are applied as the dose index which is to be the base. A dose area product value (DAP value) corresponds to the dose of radiation emitted from the radiation source. The entrance dose corresponds to the dose in the air in the absence of the patient's body (subject). The entrance surface dose corresponds to the dose in the air considering scattered radiation from the surface of the patient body (subject).

The method to calculate the cumulative dose in the cumulative dose calculating process (step S6) is as follows.

The controller 31 functions as the dose calculator. The controller 31 calculates the cumulative dose based on the dose index calculated from at least one of the imaging conditions (tubular current, tubular voltage, etc.) that is applied in the imaging and that is received from the radiation generating apparatus 1, and the distance information to the subject, and based on the number of pulses which is the number of times that the radiation generating apparatus 1 generates the radiation in the pulsed state during the imaging in order to obtain the frame image.

Here, as the dose index, the above-described DAP value, the entrance dose or the entrance surface dose are employed. For example, the entrance surface dose according to a numerical dose determination (NDD) method is employed.

The dose index can be calculated from the imaging condition and/or the distance from the subject, and the calculation can be performed before imaging. When the distance from the subject is used, the dose index can be calculated more accurately by providing an apparatus to measure the distance from the radiation source to the subject (laser ranging device, etc.) in the radiation imaging system 100.

The controller 31 is able to calculate the dose index before imaging and to display an estimated value of the dose index on the display 34 of the console 3. For example, if there is a large difference from DRLs or a standard value set for the facility, and if there is a large difference from the past imaging with the same patient, it is possible to realize the error in the imaging condition before imaging by notification on the screen of the display 34 of the console 3 or by notification by sound.

The controller 31 accumulates the dose index for the number of pulses in which the imaging is performed and calculates the cumulative dose. Here, preferably, only the number of pulses that actually hit the subject is used in the calculation of the dose index but if the portion where the radiation does not actually hit the subject is small compared to the number of pulses in imaging and it is possible to consider that it is within an acceptable error range when the dose index is calculated, the process can be simplified and the number of pulses set in the imaging condition can be used in the calculation as is. The subject moving out of the frame is considered to be the reason for the difference between the number of pulses in the set value and the number of pulses (radiation) that actually irradiates the subject.

Next, the controller 31 functions as the storage controller, and the above-described radiation image, exposure index, exposure index representative value, and cumulative dose are filed associated with at least the imaged date and patient identification information and stored in the database 41 (step S7).

When the controller 31 generates the moving image obtained by dynamic imaging as a moving image file, and stores the file, the cumulative dose at the time of imaging the moving image is associated with the moving image file and the file is stored. When the still image is generated by processing the moving image, and the still image file is output but the original moving image file is not output, the cumulative dose at the time of imaging the moving image is associated with the still image file, and the still image file is stored. This is because, even if the file is the still image file, the dose irradiated to the subject is the dose when the dynamic imaging is performed. When both the original moving image and the still image (generated by image processing) are output, the cumulative dose at the time of imaging the moving image is associated with either one of the moving image file or the still image file, and the files are stored. This is performed to prevent the dose information irradiated on the patient from being output twice, and to prevent twice the dose being calculated as the irradiated dose.

The controller 31 adds the exposed dose at the time of imaging the frame image that is imaged but not filed in the cumulative dose. For example, pre-exposure to confirm the position of the subject is not included in the moving image file but the dose of the pre-exposure is also added to the cumulative dose. The dose of the frame images deleted after the dynamic imaging is also added to the cumulative dose.

According to the above embodiments, the exposure calculator that calculates the exposure index representative value of the radiation image based on the radiation image including the plurality of frame images and the exposure target setter that is able to set the target value of the exposure index different for each imaging mode are provided. Therefore, the user who refers to the imaged radiation image is able to determine within a short time whether the exposure of the string of frame images is appropriate or not by using the exposure index representative value. In addition, since the target value of the exposure index is set differently for each imaging mode, the exposure index representative value can be used to determine within a short time whether exposure is appropriate or not in light of the target value of the exposure index suitable for each imaging mode.

According to the above embodiments, the dose calculator that calculates the radiation dose in the imaging in order to obtain the radiation image including the plurality of frame images is provided. The dose calculator calculates the radiation dose equivalent to the cumulative dose of all of the imaged frames based on the dose index calculated from at least one of the imaging conditions received from the radiation generating apparatus 1 applied when the imaging is performed and the distance information between the subject, and based on the number of pulses which is the number of times the radiation generating apparatus 1 generated the radiation in a pulsed state in order to obtain the frame image when the imaging is performed. The calculation of the radiation cumulative dose becomes simple according to the above method of calculation.

Therefore, according to the above embodiments, the calculation of the radiation dose when the radiation mage including a plurality of frame images is imaged can be performed appropriately in an easy form.

Although an embodiment of the present invention is described specifically above, the embodiments of the present invention are not limited to the above, and various modifications are possible without leaving the scope of the invention.

For example, according to the above embodiment, the console 3 includes the function to perform the processes performed when the imaging is performed, but some or all of the functions performed in this process can be performed by other apparatuses included in the radiation imaging system 100 or other systems connected to the radiation imaging system 100.

The calculation technique of the exposure index is not limited to two-dimensional images and can be applied to three-dimensional images.

According to the above description, a semiconductor memory or a hard disk can be used as the computer readable medium storing the program regarding the above embodiments but the embodiments are not limited to the above.

As the computer-readable storage medium, a nonvolatile memory, such as a flash memory, and a portable storage medium, such as a CD-ROM, may also be used.

A carrier wave is also applied as the medium to provide data of the program according to the embodiments through the communication lines.

What is claimed is:

1. A radiation imaging system comprising:
a controller comprising a hardware processor; and
a storage,
wherein the hardware processor, under control of a program stored in the storage, performs processes comprising:
calculating a radiation dose applied when performing an imaging process that obtains a radiation image including a plurality of frame images, the radiation dose corresponding to a cumulative dose amount of all imaged frames in the plurality of frame images, and the radiation dose being calculated before or after the imaging process based on a dose index and a number of pulses,
wherein the dose index is calculated from at least one of (i) an imaging condition is applied when the imaging process is performed and which is received from a radiation generating apparatus, and (ii) distance information showing a distance to a subject, and
wherein the number of pulses represents a number of times that the radiation generating apparatus generates radiation in a pulsed state to obtain the frame images when the imaging process is performed.

2. A non-transitory computer-readable storage medium storing a program thereon, the program being executable to control a computer to perform processes comprising:
calculating a radiation dose applied when performing an imaging process that obtains a radiation image including a plurality of frame images, the radiation dose being equivalent to a cumulative dose amount of all of the frame images that are imaged, and the radiation dose being calculated before or after the imaging process based on a dose index and a number of pulses,
wherein the dose index is calculated from at least one of (i) an imaging condition applied when the imaging process is performed and which is received from a radiation generating apparatus, and (ii) distance information showing a distance to a subject, and
wherein the number of pulses represents a number of times that the radiation generating apparatus generates radiation in a pulsed state to obtain the frame images when the imaging process is performed.

* * * * *